United States Patent
Bancroft et al.

[11] Patent Number: 6,040,144
[45] Date of Patent: *Mar. 21, 2000

[54] PROCEDURE FOR PREPARING GENE EXPRESSION LIBRARIES ENRICHED FOR SECRETORY PROTEIN GENES

[75] Inventors: Frank Carter Bancroft, Huntington; Makiko Fliss, New York, both of N.Y.

[73] Assignee: Mount Sinai School of Medicine, New York, N.Y.

[*] Notice: This patent issued on a continued prosecution application filed under 37 CFR 1.53(d), and is subject to the twenty year patent term provisions of 35 U.S.C. 154(a)(2).

[21] Appl. No.: 08/900,347

[22] Filed: Jul. 25, 1997

[51] Int. Cl.[7] .............................. C12Q 1/68; C12N 15/63
[52] U.S. Cl. ............................................. 435/6; 435/320.1
[58] Field of Search .................................. 435/320.1, 5, 6

[56] References Cited

U.S. PATENT DOCUMENTS

| | | | |
|---|---|---|---|
| 5,536,637 | 7/1996 | Jacobs .......................................... | 435/6 |
| 5,654,173 | 8/1997 | Jacobs et al. ........................... | 435/69.1 |

OTHER PUBLICATIONS

Entenmann and Hauner, 1996, Am. J. Physiol. 39: C1001–C1006.
Pribyl and LeBien, 1996, Proc. Natl. Acad. Sci. U.S.A. 93: 10348–10353.
Wabitsch et al., 1996, Metabol. 45: 34–42.
Dittel and LeBien, 1995, J. Immunol. 154: 58–67.
el–Yazidi et al, 1995, Anticancer Res. 15: 783–790.
MacDougald et al., 1995, Proc. Natl. Acad. Sci. U.S.A. 92: 9034–9037.
Maruo et al., 1995, Reprod. Fertil. Dev. 7: 1465–1470.
Bendall et al., 1994, Exp. Hematol. 22: 1252–1260.
Winter et al., 1994, Annu. Rev. Immunol. 12: 433–455.
Larrea et al., 1993, J. Steroid Biochem. Mol. Biol. 46: 497–505.
Marks et al., 1993, Bio/Techol. 11: 1145–1149.
Maruo et al., 1992, J. Clin. Endocrinol. Metab. 754: 1362–1367.
Meilin et al., 1992, Immunol. 77: 208–213.
Schreiber et. al., 1991, Immunol. 74: 621–629.
Wolf et al., 1991, J. Immunol. 147: 3324–3330.
Hauner et al., 1989, J. Clin. Invest. 84: 1663–1670.
Sabatini et al., 1982 Cold Spring Harbor Symp. Quant. Biol. 46: 807–818.
Knight and Fahey, 1981, J. Biol. Chem. 256: 3609–3611.
Petruschke et al., 1994, Int. J. Obesity 18:532–536.
Blobel and Dobberstein, 1975, J. Cell Biol. 67:835–851.
Hedrick et al, Nature, vol. 308, pp. 149–153, Mar. 8, 1994.
Kramer et al, The Journal of Biological Chemistry, vol. 269, No. 10, pp. 7255–7261, Mar. 11, 1994.

*Primary Examiner*—Terry McKelvey
*Attorney, Agent, or Firm*—Baker Botts

[57] ABSTRACT

The present invention relates to a method for producing a gene expression library enriched for a particular class of genes comprising (i) a nucleic acid preparation step and (ii) a polyclonal antiserum screening step, wherein both steps define the class of genes of interest. The method of the invention, using selection procedures directed not only at the underlying nucleic acid but also a functional attribute of the target class of proteins, may be used to produce gene expression libraries enriched for genes encoding a desired class of proteins, including, but not limited to, secretory proteins, cell cycle associated proteins, proteins defined by a particular subcellular location, tissue specific proteins, infection-related proteins, and non-infectious disease associated proteins.

8 Claims, 1 Drawing Sheet

PROCEDURE FOR PREPARING GENE
EXPRESSION LIBRARIES ENRICHED FOR
SECRETORY PROTEIN GENES

The present invention relates to an improved method for preparing gene expression libraries representative of a functionally defined class of genes. In a preferred, nonlimiting example, the present invention provides for a method of preparing an expression library enriched for genes encoding secretory proteins, as well as the library so produced.

BACKGROUND OF THE INVENTION

In view of the current initiative to characterize the genomes of humans and other organisms, there is a need for methods of producing gene expression libraries representative of classes of genes of interest, in that non-specific libraries are associated with numerous inefficiencies. To date, gene expression libraries have generally been created using, as the specificity determining factor, nucleic acid selected as being representative of the desired class of genes.

For example, to prepare a tissue specific gene expression library, mRNA was prepared from the tissue of interest, converted into cDNA and inserted into an appropriate expression vector. To eliminate genes shared among tissues, the mRNA may have been annealed with cDNA from another tissue and the resulting hybrids removed prior to incorporation into the expression vector. The finished expression library could then be screened with an antibody directed toward the product of a specific gene of interest. Similar methods were used to prepare libraries using nucleic acid defined by other characteristics, for example, nucleic acids present in virally infected cells, or associated with a particular phase of the cell cycle. The problem with these techniques is that the selection techniques do not satisfactorily assure that non-specific genes are eliminated or, conversely, that class specific genes are not lost.

It would be of particular interest to produce a gene expression library enriched for secretory proteins. Most clinically significant proteins are secreted by their tissues of origin, and then exert their action at a distant location. The genes for a number of previously known secretory proteins have now been cloned and produced in a recombinant form, including, for example, growth hormone and other growth factors and cytokines, interferons, insulin, and erythropoietin. However, it is highly likely that a large number of clinically significant proteins remains to be identified.

It has long been known that the mRNAs for secretory proteins are associated, virtually exclusively, with membrane-bound polysomes contained in the "rough microsome" cellular fraction (Blobel and Dobberstein, 1975, J. Cell Biol. 67:835–851). The specific information for this association is contained within a "signal sequence" in the N-terminus of the nascent protein, which thus tags proteins for secretion or, in some cases, membrane insertion (Sabatini et al., 1982, Cold Spring Harbor Symp. Quant. Biol. 46:807–818). However, there is apparently no consensus amino acid sequence for the signal sequence contained in nascent secretory proteins. Accordingly, it has not been feasible to identify genes encoding secretory proteins by searching DNA sequence banks for DNA sequences that may represent signal sequences.

The purpose of the present invention is to provide a method for producing class-enriched gene expression libraries which defines the clonal members of the library not only by a nucleic acid selection procedure but also by antibody-based screening based on a functional attribute of the class of gene products. In preferred embodiments this method is used to create an expression library enriched for secretory proteins.

SUMMARY OF THE INVENTION

The present invention relates to a method of preparing a gene expression library enriched for genes encoding a class of proteins of interest comprising the steps of (i) preparing a cDNA expression library consisting of cDNA clones produced from mRNA enriched for sequences encoding the class of proteins; (ii) screening the cDNA expression library with a polyclonal antiserum directed toward the class of proteins; and (iii) pooling cDNA clones reactive with the antiserum.

For example, and not by way of limitation, the present invention provides for a method of preparing a gene expression library enriched for genes encoding secretory proteins comprising the steps of (i) preparing a cDNA expression library consisting of cDNA clones produced from mRNA collected from rough microsomes of a secretory tissue; (ii) screening the cDNA expression library with a polyclonal antiserum directed toward proteins secreted by the tissue; and (iii) pooling cDNA clones reactive with the antiserum. Analogous methods, using selection procedures directed not only at the underlying nucleic acid but also at a functional attribute of the proteins of interest, may be used to produce gene expression libraries enriched for a desired class of proteins. In nonlimiting embodiments of the invention, such libraries may be enriched for cell cycle associated genes, genes associated with a particular subcellular location, tissue specific genes, infection-related genes, disease associated genes, and so forth.

DETAILED DESCRIPTION OF THE INVENTION

Figure 1:
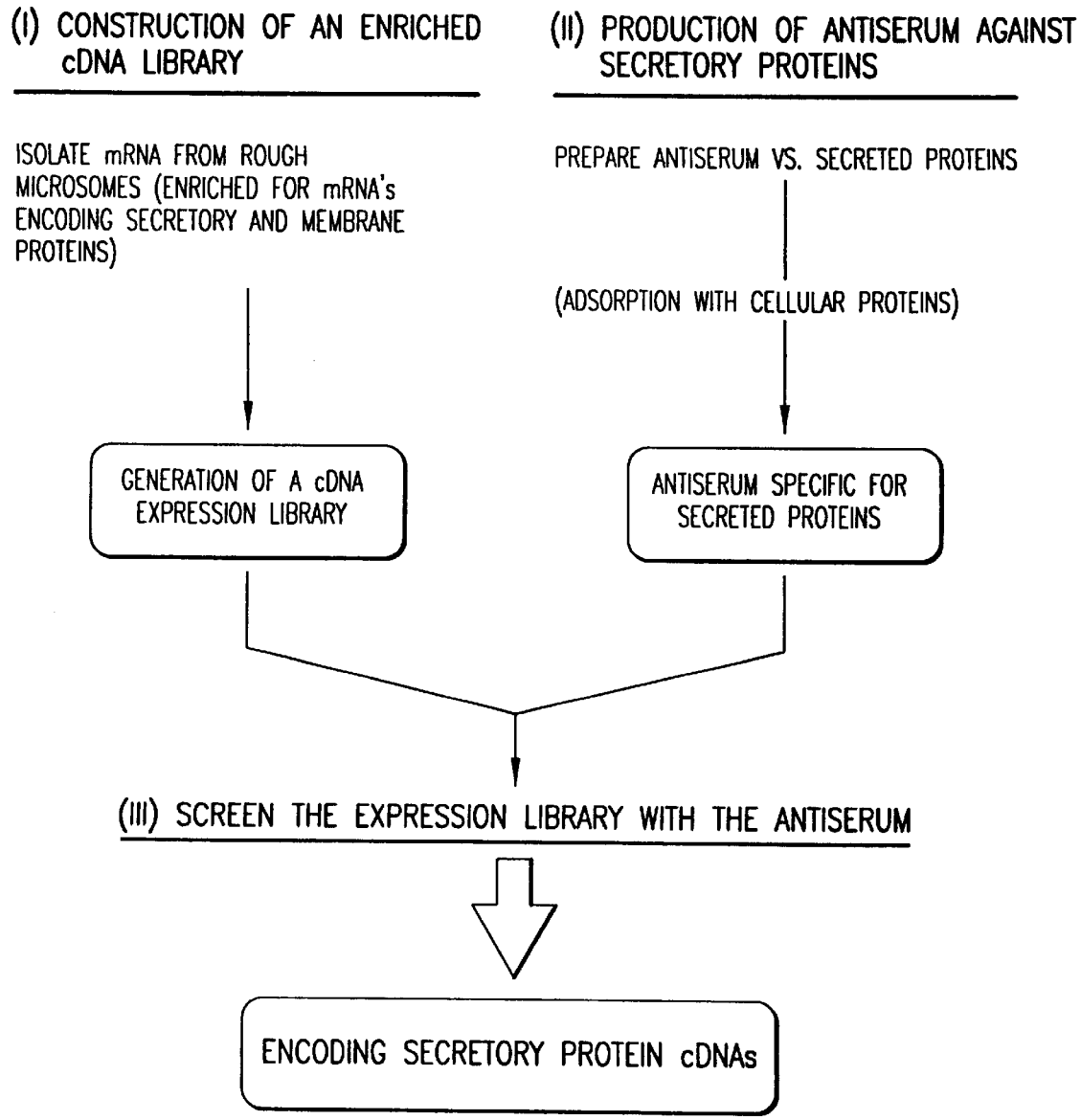
FIG. 1. Flow chart depicting the protocol according to the invention.

By way of example, and not limitation, the present invention will first be described as it relates to the preparation of a gene expression library enriched for secretory proteins. Next, enriched libraries encoding other classes of proteins will be discussed. From this disclosure, the application of the method of the present invention to additional classes of proteins will become apparent.

When the present invention is applied to produce a gene expression library enriched for genes encoding proteins secreted by a particular secretory tissue, said secretory tissue may be human or non-human in origin. Examples of secretory tissues include, but are not limited to, adipose tissue, thymus, bone, bone marrow, placenta, breast, ovary, testes, stomach, intestine, pancreas, gall bladder, liver, pituitary, adrenal gland, salivary gland and other exocrine and endocrine tissues. Cells which secrete a protein of interest are also included in the definition of secretory tissue as applied herein; for example, lymphocytes, hematopoietic stem cells, endothelial cells, platelets and cells of the nervous system which produce neurotrophic factors, endorphins and/or neurotransmitters are considered to be secretory tissue according to the invention. The use of the term "tissue" does not necessarily imply that the cells form a contiguous multicellular structure. In addition, cell lines may be used according to the invention. In a specific, nonlimiting embodiment, the human breast cancer line MDA-MB-231, as described in el-Yazidi et al., 1995, Anticancer Res. 15:783–790, or similar cell lines, may be used.

The first phase of the method of the present invention comprises preparing a cDNA expression library consisting of cDNA clones produced from mRNA collected from rough microsomes of the secretory tissue. The secretory tissue may be derived directly from the subject or may be a cultured explant. Rough microsomes containing membrane-bound polysomes may be prepared using any method known in the art. A nonlimiting example of such a method is set forth in Adesnik and Maschio, 1981, Eur. J. Biochem. 114:271–284. Briefly, such method would comprise the harvest of secretory tissue, tissue homogenization (optionally in the presence of an RNase inhibitor), differential centrifugation on sucrose step gradients and collection of rough microsome-containing fractions. The rough microsomes may then be subjected to a high salt wash to remove adventitiously bound free polysomes. (See also Colligan et al., eds., 1995, *Current Protocols in Protein Science*, John Wiley and Sons, Inc. New York, Unit 4). Since most of the mRNAs for intracellular proteins typically are present on free polysomes, while most of the mRNAs for secretory proteins are generally associated with membrane-bound polysomes, the fraction(s) prepared as described in the preceding paragraph may be significantly enriched for mRNAs encoding secretory proteins.

Next, mRNA may be prepared from the rough microsomes, and may be used, by standard techniques, to produce a cDNA expression library. Such a library may be constructed using various types of expression vectors, including but not: limited to a bacteriophage λ-based expression vector such as λgt11 (Ausubel et al., eds., 1996, *Current Protocols in Molecular Biology*, John Wiley and Sons, Inc., New York) or Lambda ZAP© II Vector (Stratagene), a bacterial plasmid expression vector, or a yeast shuttle expression vector (see Ausubel, 1996, supra). In one nonlimiting embodiment, the present invention provides for a rough microsome-generated gene expression library prepared using this first phase of the selection procedure and not the antibody-screening phase.

Where the second phase of the inventive method is applied, secreted proteins are prepared and then used to generate polyclonal antiserum. Such secreted proteins may be prepared from a directly obtainable biological product (for example, saliva, bile, gastrointestinal contents, etc.) or from a culture containing the secretory tissue (for example, a tissue explant culture). Where tissue explants are to be used, it should be noted that the presence of serum in the culture medium may result in severe contamination of the proteins secreted by the tissue explant, and, consequently, the generation of a highly non-specific antiserum. Therefore, it is preferred that a defined, serum-free medium be used for the incubation of explant cultures. The presence, in the incubation medium, of a limited number of defined proteins (for example, insulin in an adipose tissue explant culture) would not be expected to be problematic, both because the tissue under study may not contain mRNA encoding that defined protein and because any cDNA clones corresponding to defined proteins may be identified and removed from the product cDNA library and thereby eliminated from further consideration. Further, such a defined protein may serve as a carrier for the secreted proteins and may perform as a stabilizing agent and to inhibit their adherence to processing vessel walls. It may further be desirable to include a protease inhibitor in the explant culture, provided that care be taken that the presence of such inhibitor does not substantially impair the metabolism of the cultured tissue.

The following examples relating to explant cultures, useful for generating secretory proteins to be used in antiserum production, may also be useful in the preparation of nucleic acid according to the first phase of the method of the invention.

In one particular nonlimiting embodiment of the invention, explant cultures of adipose tissue may be prepared from mammary adipose tissue obtained during surgical breast reduction (Petruschke et al., 1994, Int. J. Obes. Relat. Metab. Disord. 18:532–536; Hauner et al., 1989, J. Clin. Invest. 84:1663–1670) or from abdominal adipose tissue (Entemann and Hauner, 1996, Am. J. Physiol. 270 (Cell Phsyiol. 39):C1001–C1016). In related nonlimiting examples, adipocytes may be prepared according to methods described by Wabitsch et al., 1996, Metabol. 45:34–42 or MacDougald et al., 1995, Proc. Natl. Acad. Sci. U.S.A. 92:9034–9037.

In another nonlimiting embodiment of the invention, thymic explants may be prepared, for example as described in Meilin et al., 1992, Immunol. 77:208–213 and Schreier et al., 1991, Immunol. 74:621–629, wherein thymic epithelial cell explants obtained from children undergoing corrective cardiovascular surgery are cultured on extracellular matrix coated culture plates in a defined serum free medium supplemented with defined growth factors.

In yet another nonlimiting embodiment of the invention, bone marrow explant cultures may be prepared. For example, a description of the preparation of such cultures may be found in Bendall et al., 1994, Exp. Hematol. 22:1252–1260 which describes the isolation of bone marrow from acute myeloid leukemia patients followed by the preparation of two types of explant cultures containing either long-term bone marrow stroma or bone marrow fibroblasts. Evidence was provided by Bendall et al. which indicates that, upon incubation in a defined serum free medium supplemented with known cytokines, either type of explant culture may release factors capable of inhibiting leukemic cell death and/or in maintaining clonogenicity of malignant myeloid progenitors. In other examples, bone marrow explant cultures are described in Pribyl and LeBien, 1996, Proc. Natl. Acad. Sci. U.S.A. 93:10348–10353; Wolf et al., 1991, J. Immunol. 147:3324–3330 and Dittel and LeBien, 1995, J. Immunol. 154:58–67, which relate to the isolation, from bone marrow obtained from aborted fetuses, of explant cultures of B cell precursors, hematopoietic stem cells, and bone marrow stromal cells, and the incubation of the cells in defined serum free medium. Gene expression libraries obtained from such cells may be useful toward isolating a gene encoding a hitherto unidentified soluble factor which acts in concert with interleukin-7 to promote the growth of CD10+/surface IgM$^-$ cells.

In a further nonlimiting embodiment of the invention, placental tissue explant cultures may be prepared as described in Mauro et al., 1992, J. Clin. Endocrinol. Metab. 75:1362–1367; Mauro et al., 1995, Reprod. Fertil. Dev. 7:1465–1470 and Larrea et al., 1993, J. Steroid Biochem. Mol. Biol. 46:497–505, which relate to the preparation of placental explants from trophoblastic tissues obtained from human placentas and incubation of the cells in a defined serum free medium supplemented with known growth factors.

Secreted fluid or culture medium from explant cultures may then be collected in the presence of appropriate protease inhibitors (such as serine protease inhibitors (e.g., PMSF), thiol protease inhibitors (e.g., leupeptin) and/or acidic protease inhibitors (e.g., pepstatin)) and subjected to centrifugation (for example, at 60,000×g for one hour to yield an "S-100", supernatant), and thus remove any tissue and/or cellular debris such as membranes released by any degraded tissue and/or cells. The population of secreted protein may then be concentrated using any standard procedure (e.g., filtration through an Amicon filter, or acetone precipitation followed by centrifugation). If the defined serum-free medium employed for a particular application contains a sufficiently high concentration of a particular defined protein(s), the presence of such a protein(s) may interfere with either the above concentration step and/or the production of antibodies against the proteins secreted by the tissue employed. In that case, it may prove advantageous to remove one or more of these defined protein(s) prior to the concentration step, employing a technique for specifically removing such a protein. This may be done a number of ways, including, for example, use of an affinity procedure employing either immobilized antibodies specific for that protein, or a chemical reagent displaying a degree of specificity for the defined protein(s). An example of such a specific chemical reagent that may prove useful is blue Sepharose (Pharmacia Biotech), which has been employed for purification of interferon from a serum-free medium (Knight and Fahey, 1981, J. Biol. Chem. 256:3609–3611).

Standard immunological techniques, such as those described in Harlow and Lane (1988, *Antibodies: A Laboratory Manual*, Cold Spring Harbor Laboratory, New York) may then be employed to prepare antiserum to the secreted proteins. For example, but not by way of limitation, it may be desirable, in order to improve the immune response in an innoculated animal to the secreted proteins, to couple the secreted proteins to an appropriate carrier protein (as described, for example, at p. 77 of Harlow and Lane, supra) and/or to effect limited protease digestion of the secreted proteins. Next, one or more standard laboratory animals may be immunized with secreted proteins and antiserum may be recovered (see, for example, Chapter 5 of Harlow and Lane, supra). The success of antibody preparation may be evaluated by comparing the patterns of (i) immunoblots of the secreted protein population obtained using the antiserum as a probe (see Chapter 12 of Harlow and Lane, supra) with (ii) the pattern observed when the secreted protein population is subjected to gel electrophoresis under the same conditions used in (i), and then visualized by a detection technique such as silver staining.

Alternatively, antibodies against the secreted protein fraction may be prepared by phage display technology (see, for example, Winter et al., 1994, Annu. rev. Immunol. 12:433–455; Marks et al., 1993, Bio/Technol. 11:1145–1149). Such technology permits the selection, from an antibody fragment gene recombinant bacteriophage library prepared from natural or synthetic antibody gene repertoires, of bacteriophage expressing an antibody fragment against a particular antigen. As a specific, nonlimiting example, the secreted protein fraction may be used to screen an antibody fragment gene recombinant bacteriophage library. Clones identified could then be recovered. False positives could be reduced or eliminated, for example, by preadsorbing the library with a preparation of intracellular or integral membrane proteins (i.e., non-secretory proteins) or by retesting recovered clones for reactivity with non-secretory proteins, wherein such reactive clones are discarded. Antibody fragments produced by the bacteriophage clones could then be expressed in bacteria and recovered and then employed, either individually or as a pool of antibody fragments, for the screening of the cDNA expression library.

It may be noted that it is possible that an antiserum may not contain antibodies against all the secreted proteins. However, the success in raising antibodies against at least some of the proteins secreted by the tissue may be examined both by the procedure described above and/or by testing the ability of the antiserum to detect proteins known to be secreted by the tissue. If preliminary tests of the antiserum indicate that contamination by antibodies to intracellular and/or integral membrane proteins is a problem, standard immunological adsorption techniques may be employed to remove or reduce such contaminants. This may involve, for example, adsorption of the antiserum with an acetone powder prepared from intracellular and/or integral membrane proteins, such as is described on pages 632–633 of Harlow and Lane (supra).

Next, the cDNA expression library prepared according to the first phase of the invention may be screened with the antiserum directed toward proteins secreted by the tissue. There presently exist standard procedures for employing antiserum directed against a single protein to screen a cDNA library for a clone(s) corresponding to that protein (for example, the procedure for screening a bacteriophage cDNA expression library described in Unit 6.7 of Ausubel et al., eds., 1996, *Current Protocols in Molecular Biology*, John Wiley and Sons, Inc., New York). Such methods may analogously be applied to identify clones which react with the polyclonal antiserum directed against the population of secreted proteins. Recombinant cDNA clones observed to react with the antiserum, but not with preimmune serum from the same animal(s), may be selected for further use, and preferably may be retested to ascertain selective reactivity. Clones exhibiting a positive reaction may then be pooled, and then collectively represent a gene expression library enriched for genes encoding secretory proteins.

In a further nonlimiting embodiment, a protein expressed by one of the clones reactive with the polyclonal antiserum may then be used to select, from the antiserum, antibodies specifically directed toward that protein, by a modification of the standard procedure as described on pages 312–315 of Harlow and Lane (supra) for immunoaffinity purification of antibodies on an antigen column.

In yet other embodiments of the invention, polyclonal antiserum prepared as set forth above may be used to screen a standard cDNA library (e.g., one which has not been enriched for sequences encoding a specific class of proteins, as set forth above). Reactive clones may then be pooled to create a single-tier enriched library. Such methods may be appropriate where enrichment at the nucleic acid level is problematic.

It should also be noted that an antiserum may be designed, according to the invention, to react with clones expressing proteins that are to be selected against, and then used to produce a library expressing proteins which are not recognized by the antiserum.

From the foregoing nonlimiting example of how the present invention may be applied to obtain a gene expression library enriched for genes encoding secretory proteins, the variation of the inventive method for obtaining expression libraries enriched for genes encoding other specific classes of proteins would be readily apparent to the skilled artisan.

As a first nonlimiting example, a gene expression library may be prepared which is enriched for proteins associated with a particular stage of the cell cycle. mRNA may be prepared from a synchronized population of cells at a desired point in the cell cycle. Optionally, mRNAs representing constitutively expressed genes may be removed by selective hybridization with mRNA (or corresponding cDNA) collected from cells at another stage of the cell cycle. mRNA from the stage of the cell cycle of interest may be used to prepare a cDNA expression library. Further, proteins may be prepared from a synchronized population of cells at the same stage of the cell cycle, and used to generate an antiserum. It may be desirable to remove antibodies reactive with constitutive proteins by adsorption of the antiserum with proteins prepared from cells at one or more different stages of the cell cycle. The resulting antiserum may then be used to select clones from the cDNA library for incorporation into a library enriched for cell-cycle associated genes. A similar approach may be used to produce a library enriched for genes associated with apoptosis.

As a second nonlimiting example, the present invention may be used to prepare a gene expression library associated with a particular subcellular location. For example, mRNAs encoding proteins having nuclear localization signals may be identified by the presence of nucleic acid sequences corresponding to such signals, and then used to produce a cDNA expression library. Antiserum may be prepared toward nuclear proteins and then used to select cDNA clones which, taken together, constitute a library enriched for genes encoding nuclear proteins. Of note, it may be problematic to prepare a cDNA library enriched for clones encoding nuclear proteins. However, a polyclonal antiserum may be prepared against nuclear proteins and then used to screen a general cDNA expression library prepared using nonselected mRNAs.

As a third nonlimiting example, the present invention may be used to produce a gene expression library enriched in tissue specific proteins. mRNA may be prepared from the tissue type of interest; optionally, constitutively expressed mRNAs may be removed by selective hybrization to mRNA (or corresponding cDNA) from cells of a different type of tissue; and a cDNA expression library may be prepared. Proteins prepared from the tissue may then be used to raise an antiserum (which is optionally preadsorbed with proteins from a different tissue), and the antiserum may be used to select cDNA clones and thereby create a library enriched for tissue specific genes. An analogous method may be used to produce a library enriched for genes active during a particular developmental stage.

As a fourth nonlimiting example, the present invention may be used to produce a gene expression library enriched for genes encoding proteins expressed by an infectious agent. Nucleic acid may be produced from the infectious agent itself or from a cell or organism infected with the infectious agent (optionally, and where appropriate, nucleic acids not associated with the infectious agent or infection may be removed by selective hybridization), and used to prepare a cDNA library. Proteins from the infectious agent or from a cell or organism infected with the infectious agent may then be harvested and used to raise an antiserm (which may optionally be preadsorbed with proteins not associated with the infectious agent or infection). The antiserum may then be used to select cDNA clones and thereby produce a library enriched in genes encoding proteins expressed by the infectious agent or associated with infection.

As a fifth nonlimiting example, the present invention may be used to prepare a gene expression library enriched for genes associated with a non-infectious disease. mRNA may be prepared from a diseased cell, tissue, or organism (optionally mRNAs not associated with the disease may be removed by selective hybridization with mRNA (or corresponding cDNA) from a cell, tissue or organism which is not afflicted with the disease), and may be used to produce a cDNA expression library. Protein may be prepared from a diseased cell, tissue, or organism and used to raise an antiserum (which may optionally be preadsorbed with proteins prepared from a cell, tissue, or organism not afflicated with the disease) and the antiserum may be used to select clones which may be assembled to form a gene expression library enriched for disease-associated genes.

Similar methods may be used to prepare libraries enriched for genes associated with a particular developmental stage, aging, tissue and/or cellular damage or stress, genes induced by exposure of cells or tissues to hormones or other inducing agents, genes repressed by exposure of cells or tissues to hormones or other repressor agents, and genes induced (or repressed) by the expression of genes introduced by an infectious agent or by oncogenesis. Also, various cell types may be used according to the invention, including cells or cell lines of non-secretory tissues such as, for example, but not by way of limitation, heart or striated muscle.

Other applications of the present invention would be readily apparent to the skilled artisan.

Various references are cited herein, the contents of which are hereby incorporated by reference in their entireties.

What is claimed is:

1. A method of preparing a gene expression library enriched for genes encoding secretory proteins comprising the steps of (i) preparing a cDNA expression library consisting of cDNA clones produced from mRNA collected from rough microsomes of a secretory tissue; (ii) screening the cDNA expression library with a polyclonal antiserum directed toward proteins secreted by the tissue; and (iii) pooling cDNA clones reactive with the antiserum.

2. The method according to claim 1 wherein the secretory tissue is an adipose tissue.

3. The method according to claim 1 wherein the secretory tissue is an endocrine or paracrine tissue.

4. The method according to claim 1 wherein the secretory tissue is a hematopoetic tissue.

5. A gene expression library enriched for genes encoding secretory proteins prepared by a method comprising the steps of (i) preparing a cDNA expression library consisting of cDNA clones produced from mRNA collected from rough microsomes of a secretory tissue; (ii) screening the cDNA expression library with a polyclonal antiserum directed toward proteins secreted by the tissue; and (iii) pooling cDNA clones reactive with the antiserum.

6. The library according to claim 5, wherein the secretory tissue is an adipose tissue.

7. The library according to claim 5, wherein the secretory tissue is an endocrine or paracrine tissue.

8. The library according to claim 5, wherein the secretory tissue is a hematopoetic tissue.

* * * * *